US008921771B2

(12) United States Patent
Chen et al.

(10) Patent No.: US 8,921,771 B2
(45) Date of Patent: Dec. 30, 2014

(54) CORONA DISCHARGE DEVICE AND ION MOBILITY SPECTROMETER HAVING CORONA DISCHARGE DEVICE

(71) Applicants: Nuctech Company Limited, Beijing (CN); Tsinghua University, Beijing (CN)

(72) Inventors: Zhiqiang Chen, Beijing (CN); Qingjun Zhang, Beijing (CN); Shuqiang Dong, Beijing (CN); Yuanjing Li, Beijing (CN); Ziran Zhao, Beijing (CN); Yinong Liu, Beijing (CN); Yan Zheng, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 0 days.

(21) Appl. No.: 14/005,820

(22) PCT Filed: Nov. 29, 2012

(86) PCT No.: PCT/CN2012/085544
§ 371 (c)(1),
(2), (4) Date: Sep. 17, 2013

(87) PCT Pub. No.: WO2013/079008
PCT Pub. Date: Jun. 6, 2013

(65) Prior Publication Data
US 2014/0299758 A1    Oct. 9, 2014

(30) Foreign Application Priority Data

Dec. 2, 2011    (CN) .......................... 2011 1 0396845

(51) Int. Cl.
*B01D 59/44*    (2006.01)
*H01J 49/00*    (2006.01)
*H01T 19/04*    (2006.01)
*H01J 49/26*    (2006.01)

(52) U.S. Cl.
CPC ................. *H01T 19/04* (2013.01); *H01J 49/26* (2013.01)
USPC ........................... 250/281; 250/288; 250/287

(58) Field of Classification Search
USPC .................................. 250/281–283, 287–292
See application file for complete search history.

(56) References Cited

U.S. PATENT DOCUMENTS

2002/0134932 A1*    9/2002    Guevremont et al. ........ 250/281
2012/0199088 A1*    8/2012    Burrows et al. ........... 123/143 B

FOREIGN PATENT DOCUMENTS

CN    202333446 U    7/2012
CN    202333446 U *  7/2012
EP    1178307 A1    2/2002

OTHER PUBLICATIONS

International Search Report, PCT/CN2012/085544.

*Primary Examiner* — Jack Berman
*Assistant Examiner* — Meenakshi Sahu
(74) *Attorney, Agent, or Firm* — Kinney & Lange, P.A.

(57) ABSTRACT

The present invention provides a corona discharge device, comprising a first electrode including: a first substantially cylindrical inner chamber portion and a second substantially conical inner chamber portion in communication with the first inner chamber portion, wherein the second inner chamber portion has a cross sectional area that gradually enlarges in a direction away from the first inner chamber portion. The present invention also provides an ion mobility spectrometer comprising: an ionization region; and the corona discharge device disposed in the ionization region. With the above construction and structure, the ion mobility spectrometer of the present invention has the advantages that extraction of ions is facilitated and a life time of the corona electrode is lengthened. In addition, the focusing and storing electrode is used to effectively shield interference of a corona discharge pulse, and to push and focus sample ions. A designed voltage control solution is used to achieve mobility differentiating of ions, while a corona pulse is shielded to prevent variation in an ion quantity due to the corona pulse, thereby achieving an effect of stabilizing mobility spectrum lines.

14 Claims, 3 Drawing Sheets

CORONA DISCHARGE DEVICE AND ION MOBILITY SPECTROMETER HAVING CORONA DISCHARGE DEVICE

BACKGROUND OF THE INVENTION

1. Field of the Invention

The present invention relates to a corona discharge device and an ion mobility spectrometer having the corona discharge device.

2. Description of the Related Art

An ion mobility spectrometer achieves differentiating of ions based on the fact that different ions drift at different speeds in a uniform weak electric field. The ion mobility spectrometer has the following advantages. The ion mobility spectrometer is capable of differentiating ions quickly, has a high sensitivity, does not need a vacuum environment, and facilitates miniaturization. Therefore, the ion mobility spectrometer is widely used in the field of detection of drugs and explosives. A typical ion mobility spectrometer is generally composed of a sample feeding part, an ionization region, an ion door, a drift region, a collection region, a reading circuit, a data acquiring and processing part, a control part, and the like. The ionization part mainly functions to convert molecules of a sample into ions that can be drifted so as to be separated. Therefore, the effect of ionization affects performance of the spectrometer very directly. Among current techniques, the common and widely used ionization assembly is one which employs a Ni63 radiation source. The ionization assembly has a small volume and a high stability, and does not need any additional circuit, but brings about a narrow linear range, a lower concentration of converted ions, and radioactive contamination. Especially the radioactive contamination causes much inconvenience to the operation, transportation and management of the apparatus.

One solution for overcoming the radioactive contamination is to adopt corona discharge technology instead of radiation source technology. The corona discharge is a phenomenon in which ionization of molecules of gas is caused due to a local strong electric field in a spatial nonuniform electric field. Ions generated directly by the corona discharge are generally called reactant ions. When molecules of a sample having a higher proton or electron affinity pass through the ionization region, they capture electric charge of the reactant ions so as to be ionized. Generally, a structure for the corona discharge is relatively simple and thus has a low cost, while a concentration of electric charge generated by the corona discharge is far higher than that generated by a radiation source. Therefore, the corona discharge facilitates improvement of sensitivity of the ion mobility spectrometer and obtains a large dynamic range.

However, it has disadvantages to perform ionization by using corona discharge. The corona discharge needs a high-voltage power source for supplying electric power. Furthermore, because the corona discharge itself occurs in a pulsed process (a Trichel pulse), a disorder of spectrum lines will be caused such that a detection result will be seriously affected if ions are allowed to enter the ion mobility spectrometer directly through the ion door. In addition, ions in a region of the corona discharge will be accelerated by an electric field in the region to strike a corona electrode so as to be lost. As a result, improvement of the sensitivity of the ion mobility spectrometer is inhibited. How to effectively drag out the ions from the ionization region is still a serious problem to be solved. In addition, since the corona discharge will causes oxidation of the corona electrode, it is an important problem to lengthen a life time of the electrode.

SUMMARY OF THE INVENTION

An object of the present invention is to provide a corona discharge device and an ion mobility spectrometer having the corona discharge device which can structurally lengthen a life time of an electrode.

Another object of the present invention is to provide an ion mobility spectrometer which can structurally facilitate extraction of ions.

A further object of the present invention is to provide an ion mobility spectrometer which can effectively shield interference of a corona discharge pulse by means of a focusing and storing electrode.

In accordance with an aspect of the present invention, the present invention provides a corona discharge device, comprising a first electrode including: a first substantially cylindrical inner chamber portion and a second substantially conical inner chamber portion in communication with the first inner chamber portion, wherein the second inner chamber portion has a cross sectional area that gradually enlarges in a direction away from the first inner chamber portion.

In accordance with an aspect of the present invention, the first electrode further includes: a first substantially cylindrical portion defining the first inner chamber portion; and a second substantially conical portion connected with the first portion and defining the second inner chamber portion.

In accordance with an aspect of the present invention, the first inner chamber portion has a shape of a substantially circular cylinder and the second inner chamber portion has a shape of a substantially circular cone, and the first inner chamber portion and the second inner chamber portion are substantially coaxially arranged.

In accordance with an aspect of the present invention, the first electrode further includes an opening passing through a wall of the first electrode; and the corona discharge device further comprises a second electrode inserted in an inside of the first electrode from an outside of the first electrode through the opening of the first electrode, wherein the second electrode has a shape of a needle.

In accordance with an aspect of the present invention, the second electrode is inserted in the first inner chamber portion.

In accordance with an aspect of the present invention, the second needle-shaped electrode is at least one pair of second needle-shaped electrodes disposed opposite to each other and extending on substantially the same straight line.

In accordance with an aspect of the present invention, the present invention provides an ion mobility spectrometer comprising: an ionization region; and the above corona discharge device disposed in the ionization region.

In accordance with an aspect of the present invention, the ion mobility spectrometer further comprises a focusing and storing electrode having a substantially conical skirt section, wherein at least a portion of the skirt section is inserted in the second inner chamber portion of the first electrode.

In accordance with another aspect of the present invention, the skirt section has a shape of a substantially circular cone.

In accordance with a further aspect of the present invention, the first inner chamber portion has a shape of a substantially circular cylinder, and an end of the skirt section close to the corona discharge device has a diameter smaller than a diameter of the first inner chamber portion.

In accordance with a further aspect of the present invention, the ion mobility spectrometer further comprises a first grid electrode, wherein the first grid electrode is electrically connected to an end of the skirt section of the focusing and storing electrode away from the corona discharge device.

In accordance with a further aspect of the present invention, the ion mobility spectrometer further comprises a second grid electrode, wherein the second grid electrode is separated from the first grid electrode by a predetermined distance.

In accordance with a further aspect of the present invention, the first electrode and the focusing and storing electrode are substantially coaxially arranged.

In accordance with a further aspect of the present invention, a carrier gas flows substantially in an axial direction of the first electrode in the first electrode.

In accordance with a still further aspect of the present invention, the present invention provides an ion mobility spectrometer comprising: an ionization region; a corona discharge device disposed in the ionization region, a cylindrical electrode of the corona discharge device having an inner chamber portion; and a focusing and storing electrode having a substantially conical skirt section, wherein at least a portion of the skirt section is inserted in the inner chamber portion of the electrode.

In accordance with another aspect of the present invention, the skirt section has a shape of a substantially circular cone.

In accordance with a further aspect of the present invention, the inner chamber portion has a shape of a substantially circular cylinder, and an end of the skirt section close to the corona discharge device has a diameter smaller than that of the inner chamber portion.

In accordance with a further aspect of the present invention, the ion mobility spectrometer further comprises a first grid electrode, wherein the first grid electrode is electrically connected to an end of the skirt section of the focusing and storing electrode away from the corona discharge device.

In accordance with a further aspect of the present invention, the ion mobility spectrometer further comprises a second grid electrode, wherein the second grid electrode is separated from the first grid electrode by a predetermined distance.

In accordance with a further aspect of the present invention, the electrode and the focusing and storing electrode are substantially coaxially arranged.

In accordance with a further aspect of the present invention, a carrier gas flows substantially in an axial direction of the electrode in the electrode.

With the above construction and structure, the extraction of ions is facilitated and a life time of an electrode is lengthened. In addition, the focusing and storing electrode is used to effectively shield the electrical disturbance of a corona discharge pulse, and drag and focus sample ions. A designed voltage control solution is used to achieve well separated mobility spectrum, while a stable data line is achieved by minimizing the difference of charged particle number from each corona spark.

DETAILED DESCRIPTION OF THE EMBODIMENTS

An ion mobility spectrometer according to the present invention can be operated in either positive or negative ion mode. For the purpose of convenience, embodiments of the present invention will be described hereinafter based on only the positive ion mode.

Figure 1:
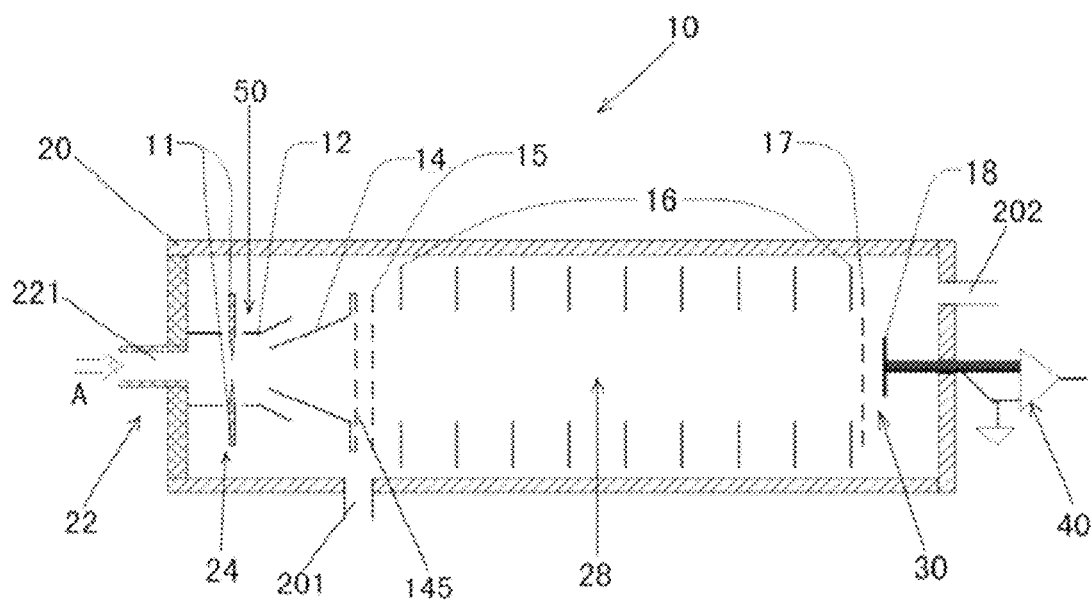
FIG. 1 is a schematic view of an ion mobility spectrometer according to an embodiment of the present invention.

FIG. 1 is a schematic view of an ion mobility spectrometer 100 according to an embodiment of the present invention. As shown in FIG. 1, the ion mobility spectrometer 100 composes a housing 20, a sample feeding part 22, an ionization region 24, a focusing and storing electrode 14, a drift region 28, a collection region 30, a reading circuit 40, a data acquiring and processing device, a control part, and the like. The sample feeding part 22 comprises an inlet 221 for introducing a carrier gas and a sample. In addition, the ion mobility spectrometer 100 further comprises a gas outlet 201 and a drift gas inlet 202. The ion mobility spectrometer 100 further comprises a corona discharge device 50 disposed in the ionization region 24; drift electrodes 16 which are disposed in the drift region 28 and are configured as coaxial circular rings arranged at equal intervals; a Faraday plate 18 disposed in the collection region 30; and an aperture grid 17 disposed between the drift electrodes 16 and the Faraday plate 18 for restraining ions from generating electrostatically induced charge on the Faraday plate 18. In an example, the aperture grid 17 is configured to be a single screen. The Faraday plate 18 is a circular flat plate, and is coupled to a charge sensitive amplifier to read an ion signal.

Figure 2:
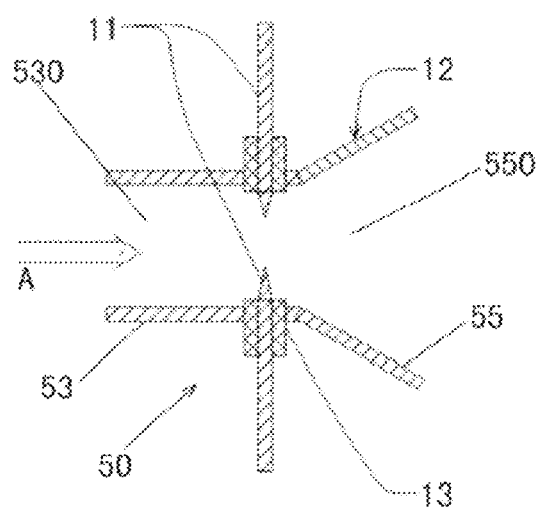
FIG. 2 is a schematic cross sectional view of a corona discharge device according to an embodiment of the present invention.
Figure 3:
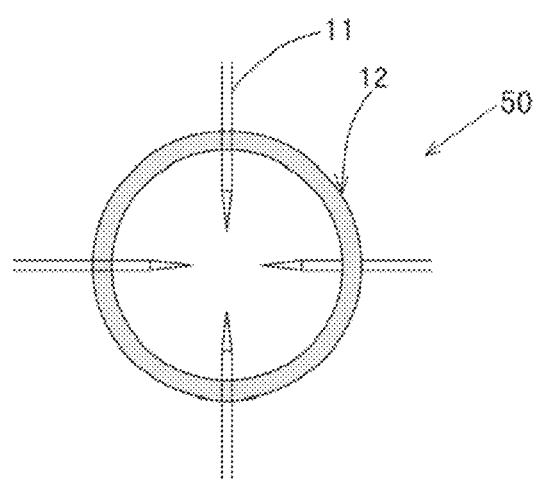
FIG. 3 is a schematic left view of the corona discharge device according to the embodiment of the present invention.
Figure 4:
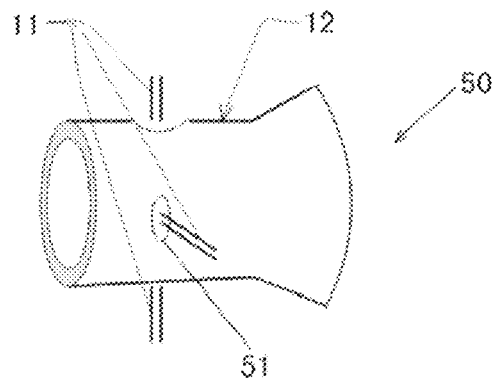
FIG. 4 is a schematic perspective view of the corona discharge device according to the embodiment of the present invention.

As shown in FIGS. 2 to 4, the corona discharge device comprises a first electrode 12 including: a first substantially cylindrical inner chamber portion 530 and a second substantially conical inner chamber portion 550 in communication with the first inner chamber portion 530. The second inner chamber portion 550 has a cross sectional area that gradually enlarges in a direction away from the first inner chamber portion 530. The first electrode 12 is substantially tube-shaped. The first electrode 12 further includes: a first substantially cylindrical portion 53 defining the first inner chamber portion 530; and a second substantially conical portion 55 connected with the first portion 53 and defining the second inner chamber portion 550.

As shown in FIGS. 1 to 4, the first inner chamber portion 530 may have a shape of a substantially circular cylinder and the second inner chamber portion 550 may have a shape of a substantially circular cone, and the first inner chamber portion 530 and the second inner chamber portion 550 are substantially coaxially arranged. The first portion 53 may have a shape of a substantially circular cylindrical surface and the second portion 55 may have a shape of a substantially circular conical surface, and the first portion 53 and the second portion 55 may be substantially coaxially arranged. The first inner chamber portion 530, the second inner chamber portion 550, the first portion 53 and the second portion 55 may also have any other appropriate shapes.

As shown in FIGS. 2 to 4, the first electrode 12 further includes an opening 51 passing through a wall of the first electrode 12. The opening 51 may pass through the wall of the first portion 53 or the second portion 55. The corona discharge device further comprises a second electrode 11 inserted in an inside of the first electrode 12 from an outside of the first electrode 12 through the opening 51 of the first electrode 12. The second electrode 11 has a shape of a needle. The second electrode may be inserted in the first inner chamber portion 530 or the second inner chamber portion 550.

As shown in FIGS. 2 and 4, the second electrode 11 is at least one pair (such as one pair, two pairs, three or more pairs) of second electrodes 11 disposed opposite to each other and extending on substantially the same straight line. Alternatively, each pair of second electrodes 11 may also be disposed to be in a staggered manner rather than being opposite to each other. The second electrode 11 may be referred to as a corona needle, while the first electrode 12 may be referred to as a corona target electrode.

As shown in FIGS. 2-4, the second needle-shaped electrode 11 may be connected to the first portion 53 through a circularly cylindrical insulating piece 13. The second electrode 11 may be extended in a radial direction of the first circularly cylindrical portion 53, and a length of a part of the second electrode 11 which is inserted in the first inner chamber portion 530 is adjustable. The second electrode 11 is made of oxidation resistant metal such as stainless steel, tungsten, nickel, and platinum. The first electrode 12 may be made of common metal and plated with nickel.

As shown in FIGS. 1-4, an inside of the first electrode 12 serves as a gas path, and a carrier gas entering the ion mobility spectrometer 10 from an inlet 221 for the carrier gas and a sample flows through the gas path. The carrier gas flows substantially in an axial direction of the first electrode 12 in the first electrode 12. In other words, a direction A in which the carrier gas flows into the ion mobility spectrometer is substantially parallel to the axial direction of the first electrode 12. The second electrode 11 enters the gas path. A direction of an electric field generated by the first electrode 12 and the second electrode 11 is orthogonal to the direction A of the carrier gas flowing in the first electrode 12 so that interference from the electric field to the electric field region located downstream from the gas path can be avoided.

Figure 5:
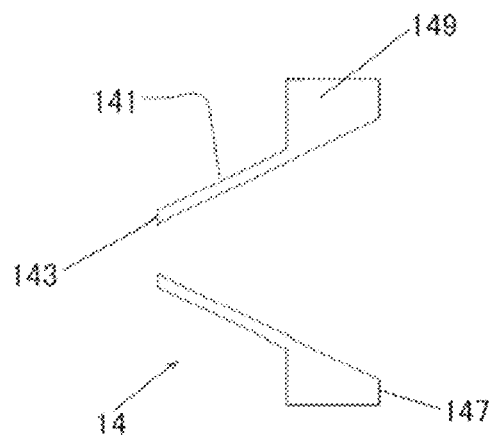
FIG. 5 is a schematic cross sectional view of a focusing and storing electrode according to an embodiment of the present invention.
Figure 6:
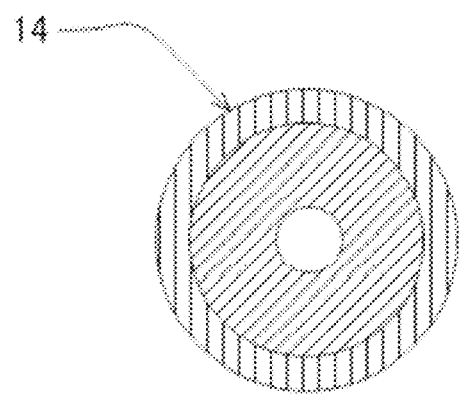
FIG. 6 is a schematic right view of the focusing and storing electrode according to the embodiment of the present invention.

As shown in FIGS. 1 and 5, the focusing and storing electrode 14 has a substantially conical skirt section 141, and the skirt section 141 may has a shape of a substantially circular conical surface. At least a portion of the conical skirt section 141 is inserted in the second inner chamber portion 550 of the first electrode 12. The skirt section 141 is not in contact with the first electrode 12. If the first electrode which is a conventional electrode and has an inner chamber is used, at least a portion of the conical skirt section 141 may be similarly inserted in the inner chamber of the first conventional electrode. The second portion 55 can enable the skirt section 141 of the focusing and storing electrode 14 to be located as close to the corona region as possible and form a focusing electric field together with the focusing and storing electrode 14. An end 143 of the skirt section 141 close to the corona discharge device 50 has a diameter smaller than a diameter of the first inner chamber portion 530 of the first portion 53 of the first electrode 12. For example, the end 143 of the skirt section 141 close to the corona discharge device 50 has a diameter about 1-3 mm smaller than a diameter of the first inner chamber portion 530 of the first portion 53 of the first electrode 12.

Alternatively, the first electrode 12 may comprise only the first substantially cylindrical inner chamber portion 530 without the second substantially conical inner chamber portion 550. In this case, at least a portion of the skirt section 141 of the focusing and storing electrode 14 may be inserted in the first inner chamber portion 530 of the first electrode 12.

The focusing and storing electrode 14 may comprise only the skirt section 141. Alternatively, the focusing and storing electrode 14 may further comprise a flange 149, and the flange 149 is formed at a larger-diameter end 147 of the conical skirt section 141. The first electrode 12 and the focusing and storing electrode 14 may be substantially coaxially arranged.

As shown in FIG. 1, the ion mobility spectrometer 10 further comprises a first grid electrode 145. The first grid electrode 145 is electrically connected to an end 147 of the skirt section 141 of the focusing and storing electrode 14 away from the corona discharge device 50. The first grid electrode 145 is in contact with the end 147 of the skirt section 141 of the focusing and storing electrode 14 away from the corona discharge device 50, or the flange 149 of the focusing and storing electrode 14. The first grid electrode 145 has a grid shape, and the lattices of the first grid electrode may have various shapes such as a hexagonal shape and a rectangular shape. A substantially equipotential region is formed inside the skirt section 141 near the end 147 or the first grid electrode 145, and the region is used for storing ions.

As shown in FIG. 1, the ion mobility spectrometer 10 further comprises a second grid electrode 15. The second grid electrode 15 is separated from the first grid electrode by a predetermined distance. The second grid electrode 15 has a grid shape, and the lattices of the second grid electrode may have various shapes such as a hexagonal shape and a rectangular shape.

The first grid electrode 145 and the second grid electrode 15 constitute the ion door. A voltage exerted across the first grid electrode 145 and the second grid electrode 15 generates a periodically-varying electric field. The periodically-varying electric field forms an ON state and OFF state of the ion door.

Figure 7:
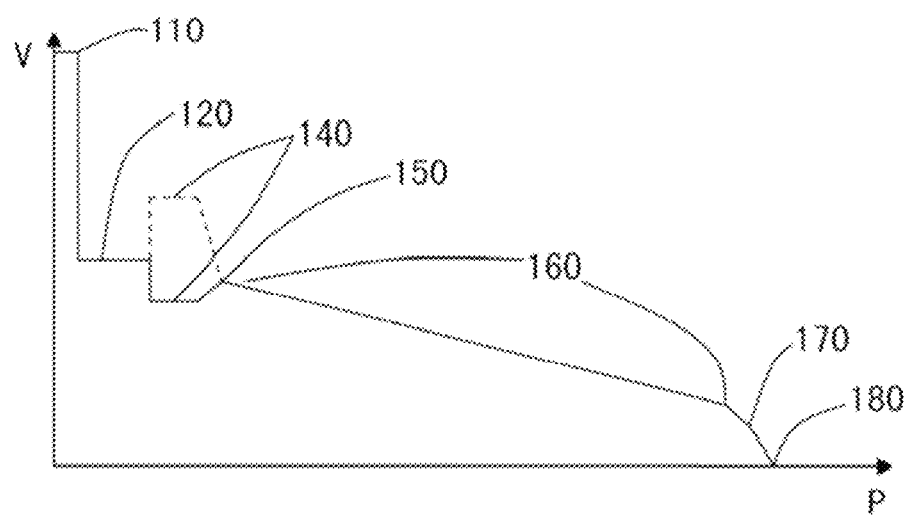
FIG. 7 is a schematic graph of electric potentials of components of an ion mobility spectrometer according to an embodiment of the present invention in a positive ion mode.

Referring to FIGS. 1 and 7, FIG. 7 is a schematic graph of electric potentials of components of an ion mobility spectrometer 10 according to an embodiment of the present invention in a positive ion mode. In FIG. 7, the axis of abscissas P denotes positions of the components, the axis of ordinate V denotes electric potentials of components, the reference numeral 110 denotes an electric potential of the second electrode 11, the reference numeral 120 denotes an electric potential of the first electrode 12, the reference numeral 140 denotes an electric potential of the focusing and storing electrode 14 and the first grid electrode 145, the reference numeral 150 denotes an electric potential of the second grid electrode 15, the reference numeral 160 denotes an electric potential of the drift electrode 16, the reference numeral 170 denotes an electric potential of the aperture grid 17, and the reference numeral 180 denotes an electric potential of the Faraday plate 18.

As shown in FIGS. 1 and 7, when the ion mobility spectrometer 10 operates, the electric potential 110 of the second electrode 11 is around 700-3000V higher than the electric potential 120 of the first electrode 12 (depending upon a radius of a tip of the second electrode 11 and a length of the second electrode 11 since different geometric sizes will result in different corona-starting voltages) to generate the corona so as to produce ions. The electric potential 140 of the focusing and storing electrode 14 periodically jumps. The focusing and storing electrode 14 is in a storage state when the focusing and storing electrode 14 is at a low electric potential (as shown by the solid line indicated by the reference numeral 140 in FIG. 7), while the focusing and storing electrode 14 is in a pushing state when the focusing and storing electrode 14 is at a high electric potential (as shown by the dashed line indicated by the reference numeral 140 in FIG. 7). When the focusing and storing electrode 14 is in the storage state, the electric potential 140 of the focusing and storing electrode 14 is 60-150V lower than the electric potential 120 of the first electrode 12, and around 5-60V lower than the electric potential 150 of the second grid electrode 15. After ions enter the focusing and storing electrode 14, they receive a weak electric field force and mainly perform thermal motion in the chamber of the focusing and storing electrode 14. Ions accumulate in the focusing and storing electrode 14 to a certain quantity after a period of time, and then the electric potential of the focusing and storing electrode 14 jumps to the pushing state. The ions generated by corona discharge at the first electrode 12 stops entering the focusing and storing electrode 14 to prevent a fluctuation in the quantity of the ions in the focusing and storing electrode 14 due to the corona pulse. The ions in the focusing and storing electrode 14 quickly enter the drift electrode 16 through the second grid electrode 15 under the action of an electric field force between the focusing and storing electrode 14 and the second grid electrode 15. In the drift electrode 16, the ions reach a stable motional state under the action of both the drag force of the electric field and a drift gas flow moving in a reverse direction. After experiencing a long drift distance, the ions with different mobility are separated from each other due to their different speeds, and finally are received by the Faraday plate 18 after passing through the aperture grid 17.

As shown in FIGS. 1 and 7, the focusing and storing electrode 14 and the first grid electrode 145 of the ion door form a combinatorial electrode. The electric potential 140 of the focusing and storing electrode 14 and the first grid electrode 145 of the ion door periodically jumps. The focusing and storing electrode 14 and the first grid electrode 145 of the ion door may be in the storage state and the pushing state depending upon the electric potential 140. When the focusing and storing electrode 14 and the first grid electrode 145 of the ion door are in the storage state (as shown by the solid line indicated by the reference numeral 140 in FIG. 7), the direction of the electric field between the first electrode 12 and the focusing and storing electrode 14 and the first grid electrode 145 of the ion door, and a moving direction of ions are the same. Since a diameter of the end 143 of the focusing and storing electrode 14 is less than the diameter of the first inner chamber portion 530 of the first electrode 12, a drifting and focusing electric field region is formed. With the drifting and focusing electric field region, the ions generated by corona are effectively dragged away from the corona region and focused into a smaller beam spot to enter the focusing and storing electrode 14. Because the focusing and storing electrode 14 and the first grid electrode 145 of the ion door are at the same electric potential and the internal electric field of the focusing and storing electrode 14 is weak, plus a weak backward electric field is exerted across the second grid electrode 15 of the ion door and the focusing and storing electrode 14 and the first grid electrode 145, a substantially equipotential region is formed at least inside the focusing and storing electrode 14 near the first grid electrode 145 of the ion door. The ions are not subjected to an electric field and main action of the ions is thermal motion in the region after the ions enter the focusing and storing electrode 14 and travel a distance. The large chamber at the end 147 of the focusing and storing electrode 14 also ensures the ions perform thermal motion and do not collide with the focusing and storing electrode 14, thereby the loss of the ions is decreased. After the ions in thermal motion accumulate to a certain quantity, however, the electric potential of the focusing and storing electrode 14 jumps to a drift state (as shown by the dashed line indicated by the reference numeral 140 in FIG. 7). As a result, the electric field between the first electrode 12 and the focusing and storing electrode 14 has a direction opposite to the moving direction of ions to prevent the ions generated by corona from entering the focusing and storing electrode 14, while the electric field between the second grid electrode 15 of the ion door and the focusing and storing electrode 14 and the first grid electrode 145 of the ion door is changed to have the same direction as the moving direction of ions. The electric potentials 160 of the circular ring-shaped electrodes 16 in the drift region 28 vary with an equal difference to form a drag electric field. The ions accumulated in the focusing and storing electrode 14 are quickly dragged into the drift region 28 by exerting a strong forward electric field by the ion door, so that the ions move towards the Faraday plate 18 at an electric potential 180, through the aperture grid 17 at an electric potential 170. As a result, the influence of variation in an ion quantity, which is caused by the corona discharge pulse, on mobility spectrum lines is weakened by an accumulation process of ions before the ion door so that the mobility spectrum lines can remain substantially stable under the corona discharge pules.

Referring to FIGS. 1 and 7, in the corona discharge device 50 as a corona discharge ion source, generally a voltage of about 700-3000V can be exerted across the first electrode 12 and the second electrode 11 to generate corona discharge. In other words, generally an electric potential difference between the electric potential 110 of the second electrode 11 and the electric potential 120 of the first electrode 12 may be about 700-3000V. Since the second electrode 11 is inserted in the first electrode 12 perpendicularly to the gas flow direction A of the carrier gas, the corona electric field is perpendicular to the gas path within the first electrode 12, thereby weakening interference (especially impulsive interference) from the corona electric field to the electric fields of the following components. In addition, several electrodes are inserted in a view to improving an ion concentration. After one of the second electrodes 11 is degraded in performance due to oxidation, the ionization property will not be caused to remarkably decrease. The first portion 53 of the first electrode 12 may have a circular cylinder shape to achieve symmetric high electric field between the first portion 53 and the second electrode 11. The second portion 55 of the first electrode 12 has a trumpet shape to allow the focusing and storing electrode 14 to be located closer to the corona ionization region, and to form a focusing electric field between the second portion 55 and the focusing and storing electrode 14. An electric potential difference between the second electrode 11 and the first electrode 12 retains close to a corona-starting voltage to avoid increasing of charge density in the ionization region, avoid generation of a great deal of molecular fragments of a sample, and lengthen a lifetime of the second electrode 11.

The invention claimed is:
1. A corona discharge device, comprising:
a first electrode including: a first substantially cylindrical inner chamber portion and a second substantially conical inner chamber portion in communication with the first inner chamber portion, wherein the second inner chamber portion has a cross sectional area that gradually enlarges in a direction away from the first inner chamber portion.

2. The corona discharge device of claim 1, wherein
the first electrode further includes: a first substantially cylindrical portion defining the first inner chamber portion; and a second substantially conical portion connected with the first portion and defining the second inner chamber portion.

3. The corona discharge device of claim 2, wherein
the first inner chamber portion has a shape of a substantially circular cylinder and the second inner chamber portion has a shape of a substantially circular cone, and the first inner chamber portion and the second inner chamber portion are substantially coaxially arranged.

4. The corona discharge device of claim 1, wherein the first electrode further includes an opening passing through a wall of the first electrode; and the corona discharge device further comprises a second electrode inserted in an inside of the first electrode from an outside of the first electrode through the opening of the first electrode, wherein the second electrode has a shape of a needle.

5. The corona discharge device of claim 4, wherein
the second electrode is inserted in the first inner chamber portion.

6. The corona discharge device of claim 4, wherein
the second needle-shaped electrode is at least one pair of second needle-shaped electrodes disposed opposite to each other and extending along substantially the same straight line.

7. An ion mobility spectrometer, comprising:
an ionization region; and
the corona discharge device of claim 1 which is disposed in the ionization region.

8. The ion mobility spectrometer of claim 7, further comprising:
a focusing and storing electrode having a substantially conical skirt section, wherein at least a portion of the skirt section is inserted in the second inner chamber portion of the first electrode.

9. The ion mobility spectrometer of claim 8, wherein
the skirt section has a shape of a substantially circular cone.

10. The ion mobility spectrometer of claim 9, wherein
the first inner chamber portion has a shape of a substantially circular cylinder, and
an end of the skirt section close to the corona discharge device has a diameter smaller than a diameter of the first inner chamber portion.

11. The ion mobility spectrometer of claim 8, further comprising:
a first grid electrode, wherein the first grid electrode is electrically connected to an end of the skirt section of the focusing and storing electrode away from the corona discharge device.

12. The ion mobility spectrometer of claim 11, further comprising:
a second grid electrode, wherein the second grid electrode is separated from the first grid electrode by a predetermined distance.

13. The ion mobility spectrometer of claim 10, wherein
the first electrode and the focusing and storing electrode are substantially coaxially arranged.

14. The ion mobility spectrometer of claim 10, wherein
a carrier gas flows substantially in an axial direction of the first electrode in the first electrode.

\* \* \* \* \*